US00PP17590P2

(12) United States Plant Patent
Benardella

(10) Patent No.: US PP17,590 P2
(45) Date of Patent: Apr. 10, 2007

(54) MINIATURE ROSE PLANT NAMED 'BENDIEZ'

(50) Latin Name: *Rosa hybrida*
Varietal Denomination: BENdiez

(75) Inventor: Frank Benardella, Englishtown, NJ (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 0 days.

(21) Appl. No.: 11/247,522

(22) Filed: Oct. 11, 2005

(51) Int. Cl.
*A01H 5/00* (2006.01)

(52) U.S. Cl. ..... Plt./122

(58) Field of Classification Search ..... Plt./122
See application file for complete search history.

*Primary Examiner*—Kent Bell
*Assistant Examiner*—June Hwu

(57) ABSTRACT

'BENdiez' is a new and distinct variety of miniature rose plant that grows two feet wide and tall with dark red flowers in proportion to the size of the foliage. Blooms are borne primarily singly, are good as cut flowers and ideal for exhibition. The color of the flowers fades very little, even though the petals become marcescent, so the plant constantly has the dark red flowers throughout the growing season. The dark green, semi-glossy foliage offers above average disease resistance in all areas of the mainland United States.

1 Drawing Sheet

CROSS REFERENCE

This new invention bears resemblance to its seed parent, 'BENmjul' (U.S. patent application Ser. No. 10/035,940, filed Dec. 21, 2001, abandoned), which is from this same breeding program. Both are miniature rose plants with dark red flowers that when open measure about 2 inches across. Both cultivars are borne singly. The most notable difference is in the plant habit. While both cultivars are upright growing plants, 'BENmjul' grows 24 to 30 inches tall and only about 15 inches wide. This new cultivar only grows about 24 inches tall and branches outward to 24 inches wide. This new cultivar also has 2 or 3 more rows of petals than 'BENmjul' and holds onto those petals longer, with its petals withering but remaining attached for up to 28 days.

A second rose from this breeding program that has the seed parent, 'BENmjul', as its pollen parent is 'BENpico' (U.S. Plant Pat. No. 16,817). There are many differences between this new invention and 'BENpico', with the most notable being that 'BENpico' has white petals edged in a red and this new invention has solid red petals. 'BENpico' is a shorter plant with smaller foliage and with smaller blooms that are borne mostly in clusters compared to the singly borne blooms of 'BENdiez'. Measured diameter of the open blooms of 'BENmjul', 'BENpico', and the new invention, 'BENdiez', show the flowers are not symmetrically round, being slightly ovate; this is not readily, visibly discernible.

RIGHTS TO THE INVENTION

Be it known that Frank A. Benardella of Englishtown, N.J., claims invention of new and useful improvements in ROSE PLANT/var. 'BENdiez' and following is a clear and exact description of the same.

Genus and species: *Rosa hybrida.*

Varietal denomination: 'BENdiez'.

BACKGROUND OF THE INVENTION

The present invention relates to a new and distinct variety of hardy, bush type plant of the miniature class. This new variety is from a single seedling created by Frank A. Benardella under controlled conditions in a greenhouse in Englishtown, N.J., by crossing the following two rose plants:

The seed parent is a dark red miniature rose, 'BENmjul' (U.S. patent application Ser. No. 10/035,940, filed Dec. 21, 2001, abandoned).

The pollen parent is a red hybrid tea, 'JACecond', (U.S. Plant Pat. No. 11,369).

The primary goal of this breeding program is to produce unique roses with award winning, hybrid tea form on plants having favorable attributes that will increase public appeal. To achieve this goal roses are selected for this hybridizing program primarily for their award winning, hybrid tea form. Pertaining to this particular cross, both parents have been noted for their exhibition form flowers that are borne one to a stem. Both are traits visible in this new invention.

As stated above, the present invention, 'BENdiez', bares resemblance to its seed parent, 'BENmjul', in color and size of the flower and being borne singly. The differences between the new invention and its seed parent, also as stated above, rest primarily in petal count and plant habit, as well as the long period of time this new invention holds onto it's shriveled petals.

Both the new invention and the pollen parent, 'JACecond', have red, exhibition form flowers, borne primarily singly, similar petal counts and the same shade of Cardinal Red on the reverse of their petals. The most obvious differences are in the sizes of the blooms and plants. The open blooms on 'JACecond' are twice the size of the two-inch open bloom on 'BENdiez'. 'JACecond' can grow up to five feet tall and four feet wide in its first year while 'BENdiez' reaches a mature height of around two feet and a width of about two feet in three years.

This new invention, 'BENdiez' is currently being sold in New Zealand and the United States. No plant protection is being filed for this plant in New Zealand.

Asexual reproduction by cuttings of this new variety in Englishtown, N.J., Rowley, Mass., and Arroyo Grande, Calif., show that all distinguishing characteristics of this rose continually come true to form.

SUMMARY OF THE INVENTION

The present invention relates to a new and distinct variety of vigorous, hardy, dwarf, bush-type rose plant of the miniature class with dark red, exhibition form flowers. The field of comparison with other dark red miniature roses is greatly reduced by combining open bloom size and petal count with plant habit and size. The one feature that distinctly differentiates this new invention from other dark red miniature roses, of which I am aware, are its marcescent petals, retaining their color while remaining attached to the receptacle for 26 to 28 days or more even though they are shriveled.

The new invention is better characterized by:

An abundance of dark red flowers that are primarily borne singly;

Mild raspberry fragrance;

An uniformly and well-branched plant that grows as wide as it does tall;

Dark green, semi-glossy foliage;

Rapid repeat of bloom cycle, appearing continuous on mature plants;

Suitability for production from softwood cuttings in pots;

A plant that grows and blooms satisfactorily both in the greenhouse and outdoors and provides outstanding decoration in the garden as a perennial, in low borders or in large containers.

BRIEF DESCRIPTION OF THE DRAWING

The larger accompanying color photograph, taken in August, shows specimens of the buds, flowers and foliage of this new variety in different stages of development.

The smaller inset was taken in July and is the top view of a flower at exhibition stage. Both are as grown under plastic in Arroyo Grande, Calif.

BOTANICAL DESCRIPTION OF THE PLANT

Following is a detailed description pertaining specifically to this new and distinct variety of miniature rose plant as observed at around 5 years of age after having been grown under plastic in Arroyo Grande, Calif., in soiless mix on a constant feed program, in plastic 8 and 10-inch nursery containers. All major colour plate identifications made are referring to The Royal Horticultural Society Colour Chart except where common terms of color definition are employed.

Genus and species: *Rosa hybrida.*
Varietal denomination: 'BENdiez'.
Market class: Miniature Rose.

FLOWERS

Blooming habit: Rapid repeat bloomer; the mature plant will have buds or flowers on it continuously throughout the growing season.

Borne: Mostly singly, occasionally with two side buds.

Bud: Form is ovate with a truncate base and an acute apex. Size just before the sepals divide is ½-inch long and 7/16-inch diameter at the widest point.

Color: When the sepals first divide the color is a Ruby Red, near 59A, or a combination of Ruby Red and Indian Lake Red, near 50B.

Sepals: There are 5 sepals, extending beyond the tip of the bud by 5/16-inch. Color of the outer surface is near 147B, a dark shade from the yellow-green group and a Scheele's Green, near 144B, just above the base and at the point of attachment to the receptacle. The appearance is matte. The inside surface is tomentose with a color near 147B, and near 144D towards the center and the base.

The 2 outer sepals are ovato-oblong with an attenuate apex and truncate base. The 3 inner sepals are ovato-acuminate with a truncate base. The margins of the 2 outer sepals are with stipitate glands and with 2 or 3 narrow foliar appendages. A few hairs and some stipitate glands can be found on the abaxial surface. The apex of one of those two outer sepals is more foliated than the rest. The size of the two outer sepals is ¼-inch wide and range from 26/32- to 27/32-inch long.

The two innermost sepals have heavily ciliate margins and a puberlant outer surface. A few stipitate glands can be found on the basal area of the outer surface only. Their size is 9/16- to 11/16-inch long and 7/32- to ¼-inch wide. They have no foliar appendages or stipitate glands along their margins.

In-between the inner and outer sepals there is a sepal with one half as the inner sepals and one half as the outer sepals except with not more than 2 foliar appendages on the foliated margin. This sepal also measure ¼-inch wide but usually is ⅝-inch long.

The sepals roll back with the petals until the outer petals are flat open and then the sepals continue rolling back until they are parallel to the stem. They remain attached to the receptacle while the hip forms.

Bloom: The blooms of the spring are 1 to 1¾-inches across and 15/16-inch deep at exhibition stage. When full open blooms are not perfectly circular, measuring 2¼- to 2½-inches by 2¾-inches across and 13/16-inch deep. Later blooms are slightly smaller, measuring 2- to 2⅛-inches by 2¼- to 2½-inches across and 11/16-inch deep and exhibition stage is only ⅞-inch deep. As the bloom opens the center is recessed by about ⅛-inch until exhibition stage and then opens with a flattened convex upper profile and a flattened lower profile. Outer edges of the petals reflex slightly and the lower profile becomes somewhat concave when the bloom is full open. Concavity increases as the petals age on the plant. The bloom has a mild to moderate fruity fragrance.

Petalage: Petal count varies between 18 and 29 with between 2 and 8 but occasionally as many as 27 petaloids. They remain fresh on the plant for 7 to 10 days at which point they begin to wither and droop but keep their color and remain firmly attached to the receptacle for up to an additional 18 days. By the 28$^{th}$ day, the petals have dropped cleanly from the plant.

Petals: Petals are thick and over-lapping. The petal surfaces are smooth with a velvety upper surface and a satiny reverse. The form of the outer petals is very broad fan shaped with a broadly obtuse base. The inner petals are obovate with an acuminate base. The margin is rounded and the apex is acute. The outermost petals measure near 1 3/16-inches wide and 1 5/32-inches long.

Color: During the first few days, at exhibition stage, the inner petals at the center of the flower are a Currant Red, near 46A, suffused with a Cardinal Red, near 53A, especially near the outer margins, and near 46B toward the base of the petals. The basal area and point of attachment are both white, near 155D. The reverse is a little lighter, near 53B, near the outer edges becoming near 53C toward the base and with a white basal area. The coloring of the outer petals is nearly the same near 46A along the outer edges while the rest of most of the petal is near 46B. The reverse is also the same as the inner petals except less of the petal is near 53B and most of it is near 53C. The color of the veins of the exposed underside of outermost petals is near 53B and the petals may have areas of Ruby Red, near 59A. The reverses of some petals have white streaks from the base of the petal going up toward the outer margin but blending in short of the margin. The white streak, when present, is usually along the central vein but may go up along other veins as well. This white streaking does not show through to the upper surface of the petals.

When half blown the upper surface of all petals is near 46B, suffused with near 46A, becoming lighter near the base, near 53C. The white basal area equals about 1/8 of the entire petal. The point of attachment of the petals has become near 11C, Naples Yellow. The reverse of the inner petals is near 60D from the red-purple group and the point of attachment is still white. The reverse of the outer petals is near 60B becoming lighter, near 60D, toward the base and near 53B bordering the margins. The point of attachment has become near 11D, Empire Yellow.

Just before the petals drop the color is near 61B from the red-purple group, becoming near 64C, a Magenta Rose, toward the base and a white basal area. The reflexed outer margins are near 60A. The reverse of the petals is near 63B, Spiarea Red, a little lighter toward the base and through the center. The basal area has become near 11D and 4D, Primrose Yellow, at attachment.

The color and appearance of the PETALOIDS is the same as the inner petals but more often with white streaks following the main vein. They measure from 1/8- to 15/32-inch wide and 7/16- to 3/4-inch long. When there are more than 15 petaloids, there will be many that are only around 1/16-inch wide and 5/32-inch long. They may be as half a petal with the white streak along one edge; there may be a yellow anther at the upper-most portion of the white streak; the white streak may proceed up through the center becoming wider as it proceeds up from the base and spreading out along the outer margin.

Receptacle: The receptacle is funnel-shaped, measuring 9/32-inch diameter and 11/32-inch tall. The color is near 144C and the surface is smooth, glossy, and pilose. The top of the receptacle is circular with a diameter of 5/16-inch and a glabrous surface. The color is a very light yellow-green, near 2-D. The alveola in the center measures 4/32- to 5/32-inch in diameter and is filled with tomentum surrounding the pistils.

Peduncle: The peduncle is strong and usually slightly curved toward the light source. The length is variable, relating to its position on the plant and the season. First spring bloom will find lengths between 2 1/16-inches and 2 3/8-inches. When there are two side buds present the length of peduncle to the main bud is around 2 7/16-inches and the side buds have peduncles of near 1 13/16-inches and 2-inches. The subsequent bloom cycles have shorter peduncles of between 1 1/8- and 1 6/8-inches with 1 1/8- and 1 3/8-inches being the most common lengths. When there are two side buds present, the main one is around 1 9/16-inches and the side ones are near 1 7/8- and 1 5/8-inches. Diameters range from 3/32- to 1/8-inch. Anthocyanin coloring is usually very weak or absent. The color is a medium yellow-green, near 146B. At the base of most peduncles is a three-leaflet leaf paired with a five-leaflet leaf. Alternatively at the base of the peduncle there may be a single, long and narrow sepalate appendage or it may have a lanceolate tip. This may be paired with another similar appendage or with a three-leaflet leaf.

General Tonality is dark red throughout the life of the flower and from a distance.

REPRODUCTIVE ORGANS

STAMENS, FILAMENTS AND ANTHERS are arranged regularly around the styles, attached to the outer rim of the receptacle. There are about 14 outermost ones measuring near 5/16-inch in length, which is longer than the rest closer to the styles, which are near 7/32-inch long. The total quantity is near 75. The color of the filaments is near 64D, Magenta Rose. The anthers are near 18D, a very pale shade from the orange-yellow group, and the pollen is darker, near 21B, Maize yellow.

PISTILS, STYLES AND STIGMAS equal just less than half the quantity of stamens. The color of the styles is closest to 59C from the red-purple group. The stigmas are white, closest to 155B.

Hips: There are no mature hips to observe at the time of the writing of this application. The diameter measures about 1/2-inch before the hips begins to change color. The surface appears semi-glossy and has a couple of hairs. At least occasionally, a couple of seeds will protrude from the top of the hip.

PLANT

The plant of the new invention is very vigorous and well branched, obtaining a height and width of 24-inches. The length of the flowering stem measures from 2-inches to 6 1/4-inches to the base of the peduncle. There are 4 to 6 five-leaflet leaves per stem. The length of the internodes ranges from 29/32-inch to 1 3/4-inches. On the flowering stems they range from 5/8-inch to 1 1/16-inches with 2 of 3 nodes around the center of the stem being equidistant.

FOLIAGE is pinnately compound with 5 leaflets and occasionally with 3 or 7. The size of the mature leaf is around 4 7/16-inches when measured along the rachis. The size of the mature terminal leaflet varies between 15/16-inch and 1 3/16-inches wide and 1 1/4- and 1 13/16-inches long. The shape of the leaflets is ovate with an oval base and acute apex. Old leaves tend toward being broadly ovate.

COLOR OF FOLIAGE is dark green. Young foliage is near 147A flushed with near 187B from the greyed-purple group. The under surface is near 147B and flushed with near 187B or 187C or both. Anthocyanin is absent on the older leaflets. The upper surface is near 147A and the under surface is between 147B and 148B.

APPEARANCE of the upper surface is semi-glossy and the under surface is matte. The central and primary lateral veins are recessed on the upper surface and protrude slightly on the under surface. Both surfaces appear glabrous but there are some single hairs along the vein on the upper surface and the basal area may be pilose. The serration is primarily simple, with a gland at the tip of each serrate and occasionally a stipitate gland in-between serrates on the basal third of the leaf.

Petiole: The length of the petioles varies between 7/16- and 5/8-inch and the diameters are around 1/16-inch. The adaxial side of the young foliage is flushed lightly with 187B from the greyed-purple group. The abaxial surface is a medium green, near 145B, and flushed lightly with near 182C from the greyed-red group. On the older leaves, the adaxial side is flushed with near 176B from the greyed-orange group. The abaxial side is near 145C. A few hairs may be found in the groove on the adaxial side. A few hairs, some glands and stipitate glands and 0 to 2 prickles may be found on the abaxial side.

Rachis: The rachis has the same coloring as the petiole. The length varies between 21/32-inch and 1 1/4-inches. Often there is a prickle on the abaxial side at the juncture with the petiolules. The adaxial surface has glands and stipitate glands along the ridges. The hairs in the groove are pilose except at the junctures with the petiolules where there is a tuft of hairs. Also along the ridge adjacent to the juncture with the petiolules there is one or more small foliar attenuate appendage.

Petiolules: The color on the young foliage is near 187B on the upper surface which continues into the leaf along the recessed veins, gradually decreasing in intensity, and near 182A on the under surface and continuing along the vein into the leaflets but fading quicker. On older foliage the color of the upper surface is near 147B, becoming much lighter, near 1D, Chartreuse Green, as it approaches the base of the leaflet and that color continuing into the leaflet along the main and primary lateral veins. The under side is closest to 145D, a very light yellow green. The length generally is near 3/16-inch to the basal leaflets when there are five leaflets on the leaf and 1/16- to 3/32-inch when there are seven leaflets. The length to the terminal leaflet varies from 21/32-inch to 1-inch. There are many stipitate glands and glandular hairs along the ridges of the upper surface with many stipitate glands where they join to the rachis and a few at the base of the leaflets. The under surface has a few hairs and a few stipitate glands near the juncture with the rachis. A small attenuate foliar appendage is located near the base of many of the petiolules and also at the base of many of the leaflets.

STIPULES measure one-third to one-half the length of the petiole. The margins lay flat, are slightly undulate and are lined with stipitate glands. There are a few narrowly lanceolate foliar appendages tipped with glands, also along the margins.

RESISTANCE to Downy and powdery mildews, black spot, rust, aphids, thrip, midge and whitefly is well above average. Resistance to spider mites is average.

Wood: Diameter of main stems varies from 7/16- to 9/16-inch, of laterals varies from 1/4- to 5/16-inch and of flowering stems is usually 1/8-inch. The color of the new wood is medium green, near 138B, and the old wood is darker, near 138A. The texture of the new wood is glabrous. Lenticels begin in near parallel lines on stems that are 2 years old or more and increase until they eventually cover the stems with a slightly rippled and relatively smooth corky surface. This lenticels area is greyed-brown between 199B and 200D. Cuttings taken from young growth of this new cultivar initiate roots in 7 to 10 days.

Prickles: Prickles are spaced at 3 to 4 per inch on all stems. They have an oblong base and are angled slightly down and may be straight or hooked. Lengths are quite variable on all stems, ranging from 1/16 inch to 3/8 inch. The color when young is nearest 181B, from the greyed-red group. Older thorns may be near 165B, or near 165A, or between 165B and 165C and the tip being near 165A, all colors from the greyed-orange group.

Hardiness: This new cultivar has been tested hardy in zones 5 through 9 with winter protection recommended for zones 6 and colder. This equates to heat tolerance zones 9 through 1.

What is claimed is:

1. A new and distinct variety of hardy, miniature rose plant is claimed, substantially as illustrated and described, with miniature, exhibition, hybrid tea form flowers of a dark red, borne mostly singly, and with dark green, semi-glossy foliage having above average disease resistance, hardy at least to zone 5.

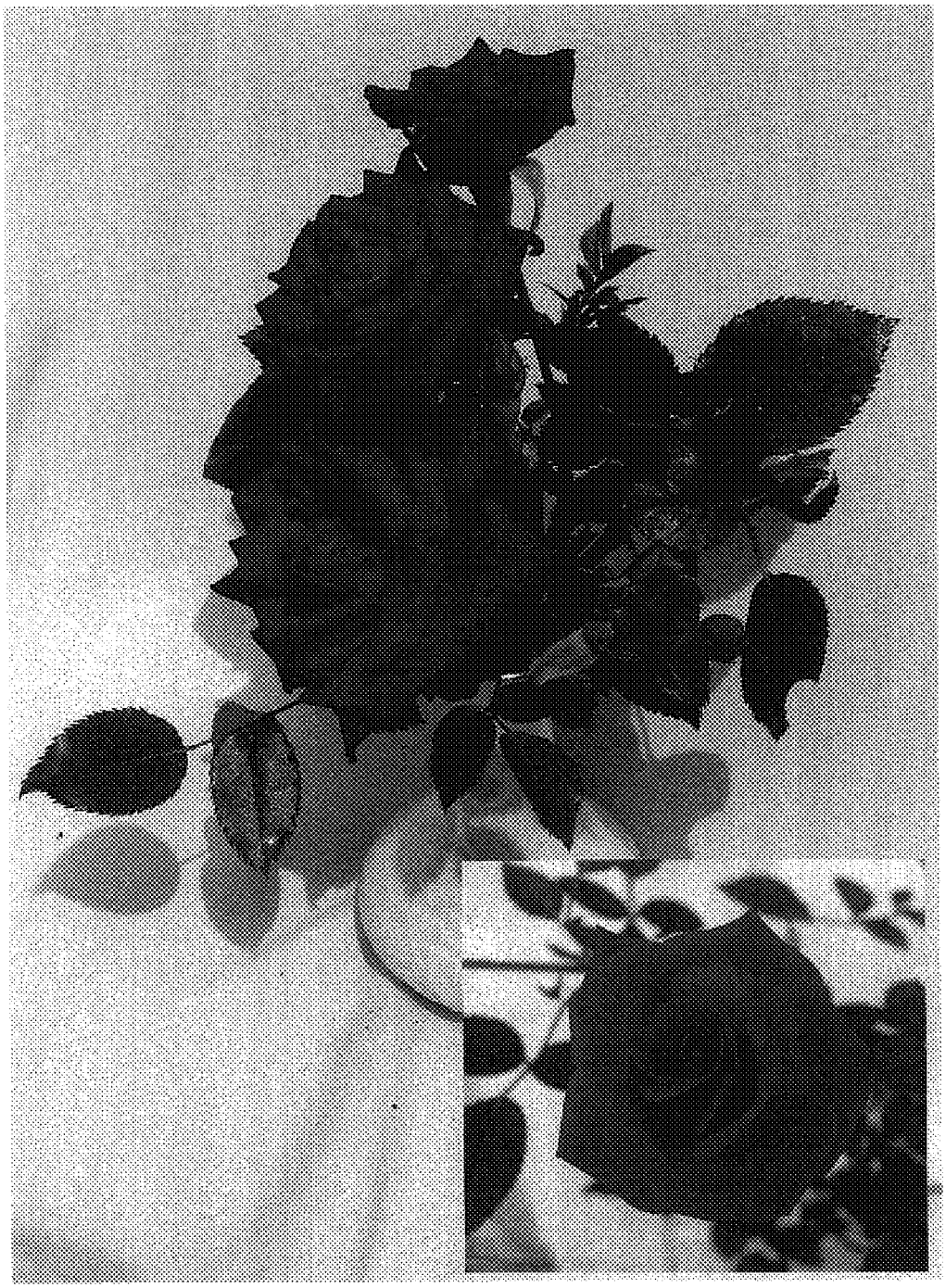

* * * * *